(12) United States Patent
Mashood et al.

(10) Patent No.: US 11,737,723 B2
(45) Date of Patent: Aug. 29, 2023

(54) MULTI-MODAL ULTRASOUND PROBE FOR CALIBRATION-FREE CUFF-LESS EVALUATION OF BLOOD PRESSURE

(71) Applicant: Healthcare Technology Innovation Centre, Chennai (IN)

(72) Inventors: Nabeel Pilaparambil Mashood, Chennai (IN); Jayaraj Joseph, Chennai (IN); Mohanasankar Sivaprakasam, Chennai (IN); Vangapandu Raj Kiran, Chennai (IN)

(73) Assignee: HEALTHCARE TECHNOLOGY INNOVATION CENTER, Chennai (IN)

( * ) Notice: Subject to any disclaimer, the term of this patent is extended or adjusted under 35 U.S.C. 154(b) by 14 days.

(21) Appl. No.: 16/765,836

(22) PCT Filed: Jun. 7, 2019

(86) PCT No.: PCT/IN2019/050438
§ 371 (c)(1),
(2) Date: May 20, 2020

(87) PCT Pub. No.: WO2019/234764
PCT Pub. Date: Dec. 12, 2019

(65) Prior Publication Data
US 2021/0093287 A1    Apr. 1, 2021

(30) Foreign Application Priority Data

Jun. 7, 2018    (IN) .............................. 201841021390
Jun. 7, 2019    (WO) ................. PCT/IN2019/050438

(51) Int. Cl.
*A61B 8/04*        (2006.01)
*A61B 8/02*        (2006.01)
(Continued)

(52) U.S. Cl.
CPC .............. *A61B 8/04* (2013.01); *A61B 5/0295* (2013.01); *A61B 5/02108* (2013.01); *A61B 8/02* (2013.01);
(Continued)

(58) Field of Classification Search
None
See application file for complete search history.

(56) References Cited

U.S. PATENT DOCUMENTS 6,176,832 B1 *    1/2001    Habu .................... A61B 5/0285
                                                                  600/485
6,261,233 B1 *    7/2001    Kantorovich ............ A61B 8/06
                                                                  600/454

(Continued)

*Primary Examiner* — Yi-Shan Yang (57) ABSTRACT

The embodiments herein provide a system for calibration-free cuff-less evaluation of blood pressure. The system includes an ultrasound-based arterial compliance probes and a controller unit connected to the said probe. The ultrasound transducers are configured to measure the change in arterial dimensions, pulse wave velocity, and other character traits of an arterial segment over continuous cardiac cycle, which is then used to evaluate blood pressure parameters without any calibration procedure using dedicated mathematical models. The pressure sensor/force sensor/bio-potential transducers/accelerometric sensors are configured to measure a pressure acting on a skin surface at a measurement site, an internal arterial transmural pressure level, an applied pressure or a hold-down pressure on the skin surface or an arterial site, biopotential and/or plethysmograph signal, arterial vibrations acting on the measurement site as a function of the arterial pressure and the mechanical characteristics and/or a function of the applied/hold-down pressure and/or function of external factors.

8 Claims, 7 Drawing Sheets

(51) Int. Cl.
  *A61B 8/00*    (2006.01)
  *A61B 8/08*    (2006.01)
  *A61B 5/021*   (2006.01)
  *A61B 5/0295*  (2006.01)

(52) U.S. Cl.
  CPC ............ *A61B 8/429* (2013.01); *A61B 8/4236* (2013.01); *A61B 8/5223* (2013.01); *A61B 8/54* (2013.01); *A61B 8/0891* (2013.01); *A61B 2562/0219* (2013.01); *A61B 2562/0247* (2013.01); *A61B 2562/043* (2013.01)

(56) References Cited

U.S. PATENT DOCUMENTS

2017/0156706 A1* 6/2017 Joseph ................... A61B 8/04
2018/0199834 A1* 7/2018 Siedenburg .......... A61B 6/4405

* cited by examiner

MULTI-MODAL ULTRASOUND PROBE FOR CALIBRATION-FREE CUFF-LESS EVALUATION OF BLOOD PRESSURE

The present application is based on, and claims priority from an International Application Number PCT/IN2019/050438 filed on 7 Jun. 2019 and Indian application 201841021390, filed on 7 Jun. 2018 the disclosure of which is hereby incorporated by reference herein.

FIELD OF INVENTION

The present invention relates to blood pressure measurement techniques, and more particularly to a method and system for calibration-free cuff-less evaluation of blood pressure using multi-modal ultrasound probes.

BACKGROUND

Blood Pressure (BP) measurement is a physiological indicator that has found wide spread use in both clinical and non-clinical settings. Usage scenario of BP poses unique functional requirements and challenges. Conventional cuff less method uses two major principles such as tonometry and pulse transit time to measure blood pressure.

In clinical practice, an applanation tonometry is often used which requires an operator to suppress arterial pulsations by externally applied pressure to capture an arterial pressure accurately. The measurement is influenced by an external applied pressure and requires skill to perform correctly. While tonometry is commonly practiced in ophthalmology, its use in measuring arterial blood pressure has remained confined mostly to tertiary clinical care settings and research applications, owing to relatively high cost of devices and skill required to perform accurate measurements.

Devices such as SphygmoCor (AtCor Medicals) utilize tonometry on radial, carotid and femoral arteries along with upper arm cuff measurements for evaluation of central aortic pressure and arterial stiffness by pulse contour analysis. A modification of tonometry principle, integrating an automated mechanism to perform applanation is referred to as vascular unloading and is used by a Finapres device. However, the measurement is performed using photoplethymography sensors on a fingertip and model based techniques are used to reconstruct brachial and aortic pressures, and calibration with an upper arm cuff is required for accurate measurements.

Pulse transit time (PTT) based techniques are the most widely researched in the area of cuff-less BP measurement. The method is based on the relation between BP and PTT, measured by evaluating the time taken by the blood pulse to propagate across a section of the arterial tree. While the basic instrumentation required for this is relatively simple, utilizing dual Photo Plethysmo Graph (PPG) waveforms or a single PPG waveform and Electrocardiography (ECG) signal, the estimation of blood pressure is often performed by model based computation that requires calibration. Most of the existing method of blood pressure measurement uses Moens-Korteweg equation and well-known empirical relationships describing the relationship between Pulse Wave Velocity (PWV), arterial stiffness indices, arterial dimensions, and blood pressure parameters. The PTT based techniques are most commonly used and hence the requirement of population and patient specific calibration limits measurement accuracy, reliability and widespread use.

Although PTT based techniques have the advantage of reduced instrumentation complexity, affordable cost and amenability for a wearable device design, the need of patient specific and/or population specific calibration to evaluate the constants used in estimation of blood pressure limits measurement accuracy and utility in practice. The requirement of an ECG measurement to accurately measure the PTT is limitation in most systems that need to be addressed to enable wide spread use of the PTT based methods. It may also be remembered that the fundamental relation between the PTT and pressure as described by the Moens-Korteweg or the Bramwell-Hill equation is valid under assumptions of elastic artery walls excited by pulsating pressure with no wave reflections. This is not the case when measurements of PTT are performed at two different points along the arterial tree that has an arterial branching in between. Further, both the viscoelastic nature of vessels and effect of wave reflections tend to affect measurements performed on a peripheral vascular tree (such as radial artery or fingertip) which is the case with most reported system.

Thus, it is desired to address the above mentioned disadvantages or other shortcomings or at least provide a useful alternative.

SUMMARY

Accordingly the embodiments herein provides a system for cuff-less blood pressure measurement of a subject, the system comprising ultrasound-based arterial compliance probes and a controller unit connected to the said probe. The said probe includes a unimodal or a bi-modal or a multi-modal arrangement of single-element ultrasound transducer with or without an integrated pressure sensor or force sensor or bio-potential transducers or accelerometric sensors. The ultrasound transducers are configured to measure a change in arterial dimensions (includes arterial diameter waveforms, minimum and maximum diameter, diameter at any given point, arterial wall thickness waveform, minimum and maximum arterial thickness values, arterial wall thickness value at any given point) pulse wave velocity, and other character traits of an arterial segment over continuous cardiac cycle, which is then used to evaluate blood pressure parameters without any calibration procedure using dedicated mathematical models. The pressure sensor/force sensor/bio-potential transducers are configured to measure a pressure acting on a skin surface at a measurement site, an internal arterial transmural pressure level, an applied pressure or hold-down pressure of the said arterial compliance probe acting on the skin surface or arterial site, a biopotential and/or plethysmograph signal, arterial vibrations acting on the measurement site as function of arterial pressure and the mechanical characteristics and/or a function of the applied/hold-down pressure and/or function of external factors acting during the measurement using said arterial compliance probe. These estimates can also be used to evaluate arterial blood pressure and stiffness indices with the help of developed mathematical models/transfer functions.

In an embodiment, the arrangement of arterial compliance probe (unimodal, dual-element probe) comprises a first ultrasound sensor and a second ultrasound sensor. Said second ultrasound sensor is separated by known fixed or variable distance from said first ultrasound sensor with 0 to 360 degree of relative angle between said first sensor and second sensor, and operated simultaneously or sequentially.

In an embodiment, further, said first sensor and second sensor are configured in parallel orientation to measure arterial dimensions of a subject by tracking the motion of said arterial wall from one ultrasound frame to a subsequent ultrasound frame. The first sensor detects arterial diameter waveform first site along said artery wall, second sensor detects arterial diameter waveform second distinct site along the artery wall; and measurement of said arterial diameter parameters (including minimum and maximum diameter values, intermediate value at any fiducial point) and local pulse wave velocity and, variation in local pulse wave velocity as function of arterial diameter or arterial pressure level from distinct fiducial points by computing time difference between said fiducial points of diameter waveform captured from said first site and second site.

In another embodiment, the arrangement of said arterial compliance probe comprises said first sensor which is arranged and placed perpendicular to said arterial wall of the subject, wherein said second sensor is configured with a relative angle (between 0 to 360 degree) with respect to the first sensor; simultaneously or sequentially measuring arterial dimensions, diameter waveforms, blood flow waveform, cross-sectional area variations, Doppler velocity and, geometrical, mechanical and flow characteristics from the said artery/arterial segments of the subject by tracking subsequent ultrasound echo frames; and used to measure arterial character traits including (but not limited to) diameter parameters and local pulse wave velocity from the measurement site of the subject.

In another embodiment, the arrangement of said arterial compliance probe (bi-modal ultrasound-pressure sensor-based design) comprises the pressure or force sensor (non-calibrated to obtain instantaneous waveforms and/or calibrated to procure instantaneous waveforms and absolute pressure/force values) arranged proximal to single-element ultrasound transducer, or configured in an array configuration (linear/curvilinear/annular).

In another embodiment, additional arrangement of said arterial compliance probe (bi-modal ultrasound-pressure sensor-based design) comprises ring-shaped pressure or force sensor (non-calibrated to obtain instantaneous waveforms and/or calibrated to procure instantaneous waveforms and absolute pressure/force values) arranged in concentric ultrasound-pressure transducer arrangement with ultrasound sensor in the middle of the concentric ultrasound-pressure transducer arrangement; or in another arrangement with pressure/force sensor in the middle of the concentric ultrasound pressure-transducer arrangement.

Further, the ultrasound-pressure transducer arrangement of arterial compliance probe performs simultaneous/sequential/continuous/periodic measurement of arterial dimensions using said single-element ultrasound transducer along with the measurement of arterial compliance probe placement pressure (on the skin surface); hold-down pressure; blood pressure acting on the skin surface; transmural blood pressure, provides feedback to the controller unit to guide operator, utilized to extract the transfer function of the tissue layer at the measurement site (between skin surface arterial segment), utilized to develop characteristic blood pressure-area curve; blood-pressure diameter curve; blood pressure-volume curve, utilized to estimate blood pressure parameters of the said subject.

Accordingly the embodiments herein provides a method and hand-held device with arterial compliance probe can be used for the evaluation of arterial dimensions including diameter parameter, arterial wall thickness and local pulse wave velocity, blood flow velocity, and Doppler velocity waveform using single-element ultrasound transducer.

In an embodiment, the evaluation of arterial blood pressure that utilizes the linear or non-linear relationship between the blood pressure values at multiple points within a cardiac cycle to the corresponding values of pulse wave velocity and diameter (or cross sectional area) at multiple points within a cardiac cycle, including but not limited to the systole and diastole points.

In an embodiment, the evaluation of arterial blood pressure which utilizes real-time measurements of arterial diameter gradient $$\left(\frac{\Delta D}{D_D}\right)$$

to evaluate the pressure gradient $$\left(\frac{\Delta P}{P_D}\right)$$

and measurements of PWV from multiple points in the cardiac cycle to estimate the arterial pressure.

In an embodiment, the evaluating arterial blood pressure by utilizing the change in pulse wave velocity from systole to diastole within a cardiac cycle, along with measurements of arterial dimensional changes for calculating an arterial pressure waveform.

In an embodiment, the evaluation of arterial BP that uses ultrasound sensors/transducers to evaluate arterial dimensions and pulse wave velocity from any artery, and employment of any of the techniques/methods for evaluation of blood pressure.

In an embodiment, the evaluation of blood pressure that utilizes the real-time changes in arterial dimensions over a cardiac cycle and simultaneous measurement of beat-to-beat heart rate/pulse rate to estimate a surrogate of cardiac output which is then calibrated to obtain an estimate of blood pressure.

Accordingly the embodiments herein provides a hand-held probe/patch probe/wearable sensor arrangement for vascular wall stiffness indices and blood pressure evaluation of a subject, comprising a patch probe configured to stick to the skin above the superficial arteries of a subject. The said probe comprises of single-element accelerometers or accelerometric sensors configured to measure the change in arterial dimensions and the acceleration associated with arterial wall displacement towards the skin surface caused by the propagation of the blood pulses wherein, said acceleration plethysmograph signal and derivatives, and/or integral of the said signal are used to develop transfer function of the tissue layer between the skin surface and the arterial site under measurement of the said subject. Extracting said transfer function of the measurement site, the system configured to measure (non-invasively and continuously) arterial vessel wall dynamics (including but not limited to arterial compliance, stiffness index, distensibility, Young's elastic modulus) and arterial blood pressure parameters of said subject locally.

In an embodiment, the patch probe/wearable sensor arrangement for vascular wall stiffness indices and blood pressure evaluation of a subject, comprising a patch probe configured to stick on the skin above the superficial arteries of a subject. The said probe has a duality (first sensor and second sensor) of accelerometers or accelerometric sensors placed at a known fixed or variable distance; configured to measure change in arterial dimensions and the acceleration associated with arterial wall displacement towards the skin surface caused by the propagation of the blood pulses from first and second arterial sites. The said first sensor and second sensor are configured to measure a local pulse wave velocity from acceleration plethysmograph signal acquired from said first measurement site and acceleration plethysmograph signal acquired from said second measurement site by computing time difference between fiducial points of acceleration plethysmograph signal captured from said first site and second site. The said local PWV and change in arterial dimensions obtained using the accelerometers or accelerometric sensors are used to measure blood pressure parameters of the subject in non-invasive and continuous manner.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

This method is illustrated in the accompanying drawings, throughout which like reference letters indicate corresponding parts in the various figures. The embodiments herein will be better understood from the following description with reference to the drawings, in which.

Figure 5:
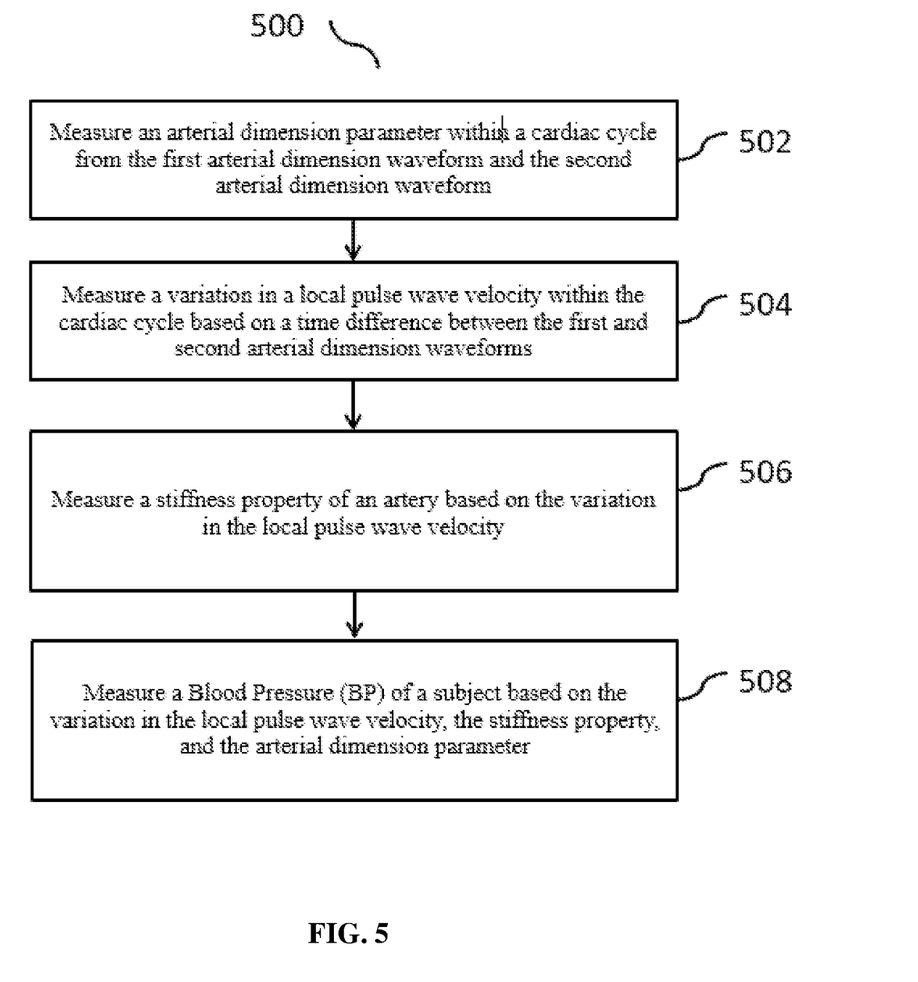
FIG. 5 is a flow diagram illustrating various operations for measuring a blood pressure of a subject, according to the embodiments as disclosed herein.

At 502, the method includes measuring an arterial dimension parameter within a cardiac cycle from the first arterial dimension waveform and the second arterial dimension waveform.

At 504, the method includes measuring a variation in a local pulse wave velocity within the cardiac cycle based on a time difference between the first arterial dimension waveform and the second arterial dimension waveform.

At 506, the method includes measuring a stiffness property of an artery based on the variation in the local pulse wave velocity.

At 508, the method includes measuring a Blood Pressure (BP) of a subject based on the variation in the local pulse wave velocity, the stiffness property, and the arterial dimension parameter.

DETAILED DESCRIPTION OF INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

As is traditional in the field, embodiments may be described and illustrated in terms of blocks which carry out a described function or functions. These blocks, which may be referred to herein as managers, units, modules, hardware components or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. Likewise, the blocks of the embodiments may be physically combined into more complex blocks without departing from the scope of the disclosure.

Referring now to the drawings, and more particularly to FIGS. 1A through 3B, where similar reference characters denote corresponding features consistently throughout the figures, there are shown preferred embodiments.

Figure 1A:
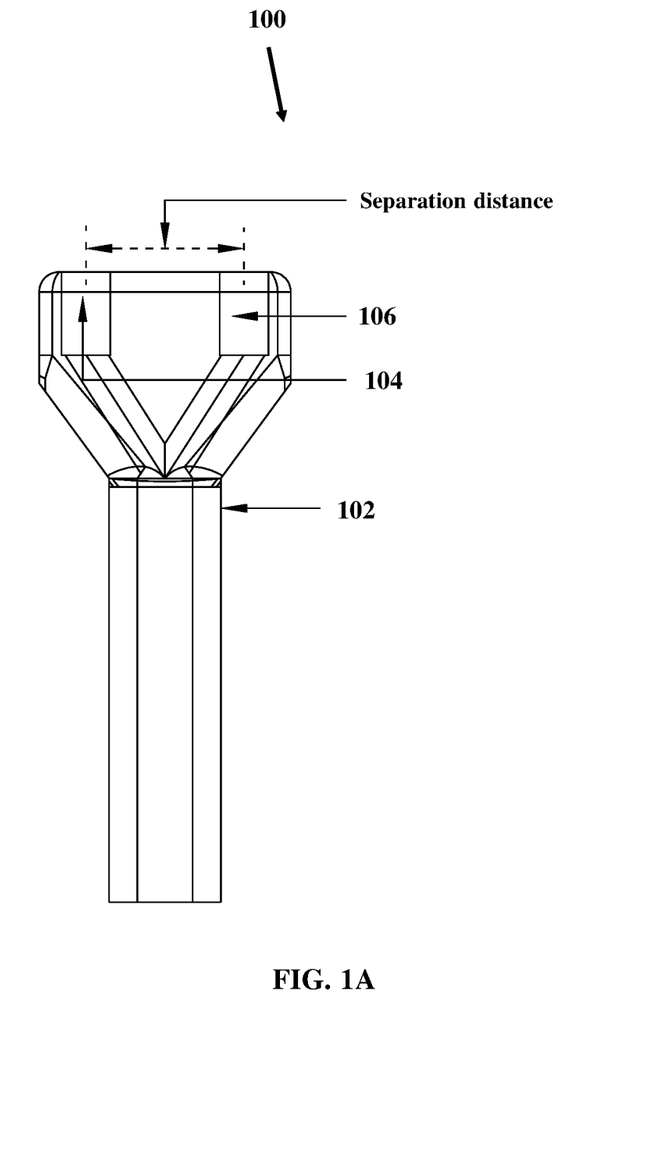
FIG. 1A and FIG. 1B illustrate a proposed probe design with unimodal/bi-modal/multi-modal arrangement, according to the embodiments as disclosed herein.
Figure 1B:
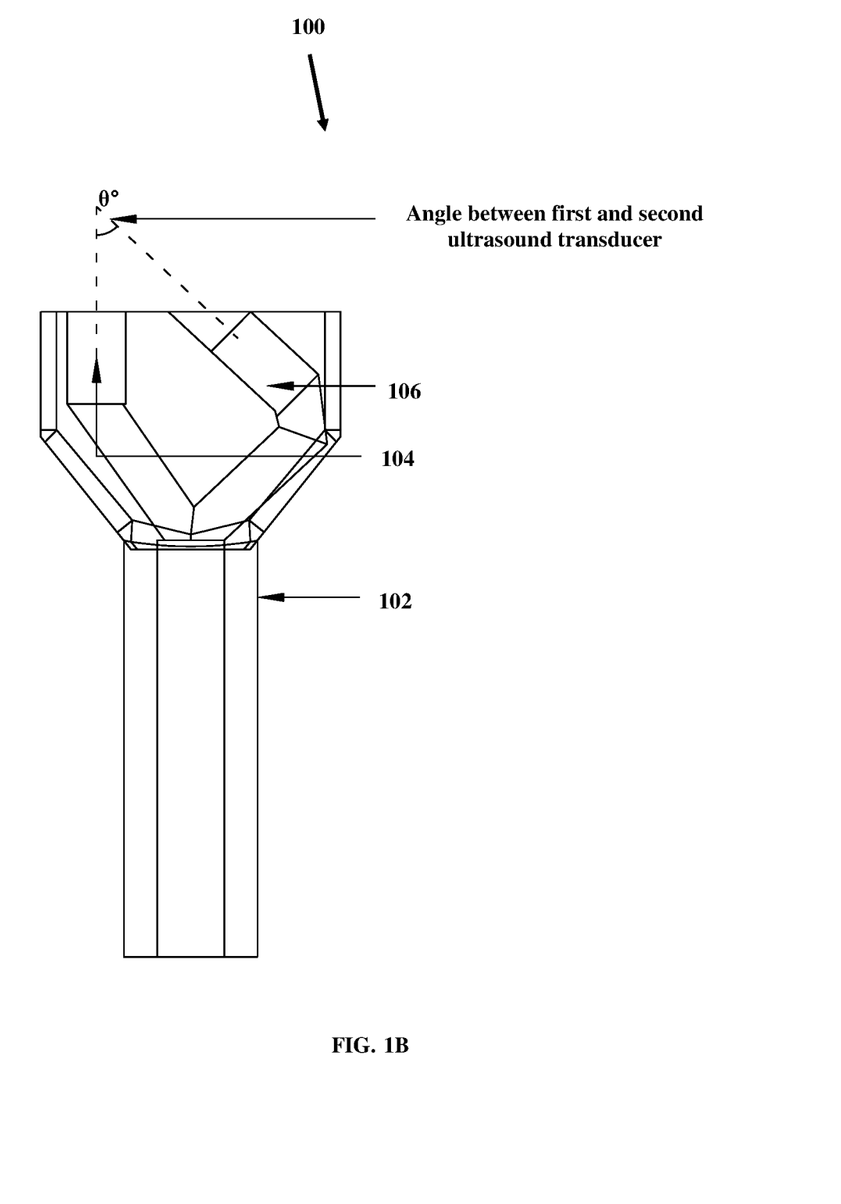

FIGS. 1A and 1B illustrates a proposed Ultrasound-based arterial compliance probes design (100) with unimodal/bi-modal/multi-modal arrangement, according to the embodiments as disclosed herein.

The ultrasound-based arterial compliance probes (100) for cuffless blood pressure measurement. The ultrasound-based arterial compliance probe (100) comprises a probe holder (102) to apply the arterial compliance probe (100) on a measurement site of the subject, a first ultrasound transducer (104), a second ultrasound transducer (106), and a controller unit. The first ultrasound transducer (104), connected at a first end of the probe holder (102), configured to measure a first arterial diameter waveform at a first fiducial point of the measurement site of the subject. The second ultrasound transducer (106), connected to a second end of the probe holder (102), configured to measure a second arterial diameter waveforms at a second fiducial point different than the first fiducial point of the measurement site of the subject.

The first ultrasound transducer (104) and the second ultrasound transducer (106) are configured in parallel orientation to measure the arterial dimensions of the subject by tracking a motion of the measurement site from one ultrasound frame to a subsequent ultrasound frame. In an embodiment, the first ultrasound transducer (104) is separated by fixed or variable distance from the second ultrasound transducer (106) with 0 to 360 degree of a relative angle between the first ultrasound transducer (104) and the second ultrasound transducer (106).

In an embodiment, the first ultrasound (104) transducer is arranged and placed perpendicular to the measurement site of the subject with 0 to 360 degree of a relative angle between the first ultrasound transducer (104) and the second ultrasound transducer (106).

In an embodiment, the first ultrasound transducer (104) and the second ultrasound transducer (106) are operated simultaneously or sequentially.

In an embodiment, the arterial dimensions comprises at least one of the diameter waveforms, blood flow waveform, cross-sectional area variations, Doppler velocity and, arterial wall thickness, geometrical, mechanical and flow characteristics from segments of the measurement site of the subject by tracking a subsequent ultrasound echo frames, a minimum and maximum diameter, a diameter at any fiducial point, an arterial wall thickness waveform, a minimum and maximum arterial thickness values, arterial wall thickness value at any fiducial point The controller unit is connected to the first ultrasound transducer (104) and the second ultrasound transducer (106) and is configured to measure arterial diameter parameter or arterial pressure level based on a time difference between the first arterial diameter waveform and the second arterial diameter waveform. Further, the controller unit is configured to measure a variation in a local pulse wave velocity based on the arterial diameter parameter or the arterial pressure level, and measure the BP of the subject based on the variation in a local pulse wave velocity.

In an embodiment, the ultrasound probe may have a single ultrasound transducer or a plurality of ultrasound transducer which will be used for real-time measurement of arterial dimensions and heart rate, for measuring a surrogate of cardiac output which would be calibrated to obtain an estimate of blood pressure. In another embodiment, the ultrasound sensor may have a plurality of elements configured in an array configuration (linear/curvilinear/annular) operated in pulse-echo as well as Doppler mode, and is used for measurement of arterial dimensional changes and blood flow velocity waveform which would be used for evaluation of blood pulse wave velocity and blood pressure.

The proposed probe design can be unimodal/bi-modal/multi-modal arrangement as shown in the FIG. 1A and the FIG. 1B. A unimodal, dual-element probe design employs two identical ultrasound transducers such as (104) and (106) (or any other measurement modalities such as photoplethysmography that can capture instantaneous or minimum to maximum arterial diameter/cross-sectional area/volume changes) arranged at a known fixed or variable distance. The relative angle between the sensing elements (the first ultrasound transducer (104) and the second ultrasound transducer (106)) can vary between 0 to 360 degree. Signal acquisition sensors are interfaced to a dual-channel/multi-channel hardware system. This arrangement can be used to simultaneously or sequentially acquire arterial diameter waveforms, the blood flow waveform, cross-sectional area variations, Doppler velocity and other related geometrical, mechanical and flow characteristics/parameters from any arterial segments.

Figure 2A:
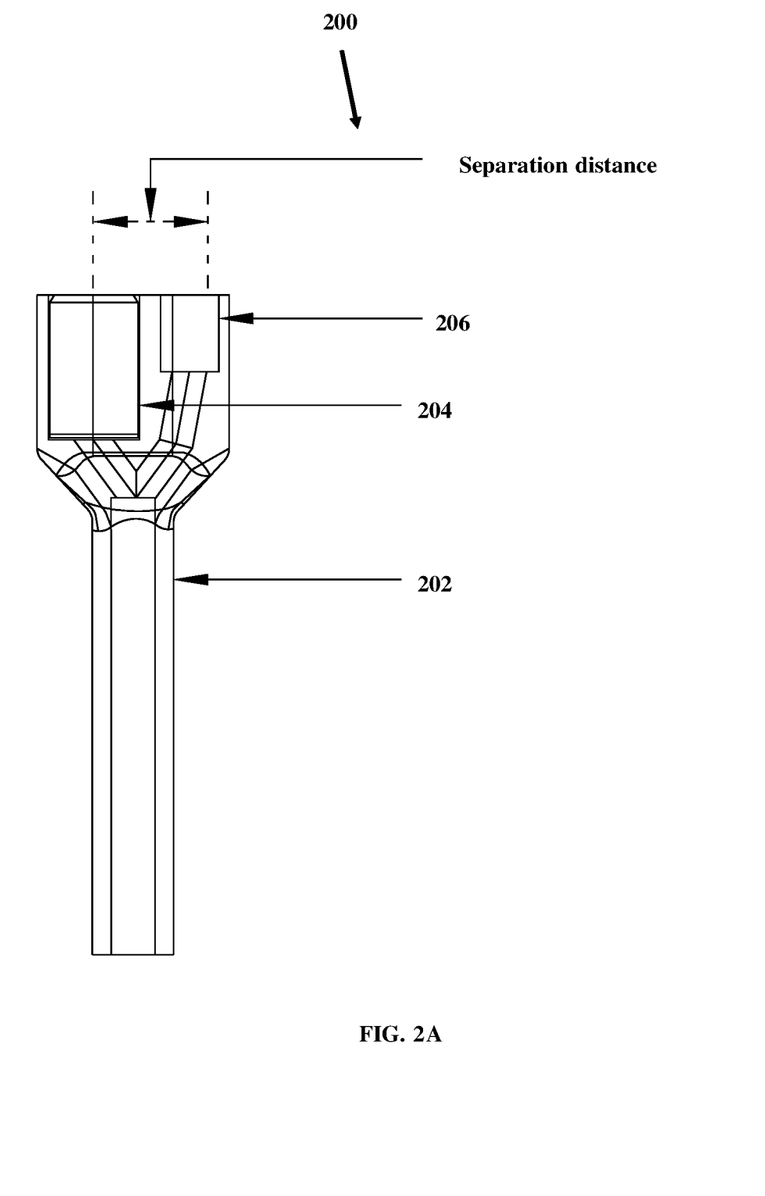
FIG. 2A illustrates a side view of a proposed bi-modal ultrasound-pressure sensor based arterial compliance probe, according to the embodiments as disclosed herein.

FIG. 2A illustrates a side view of a proposed bi-modal ultrasound-pressure sensor based arterial compliance probe (200), according to the embodiments as disclosed herein.

Figure 2B:
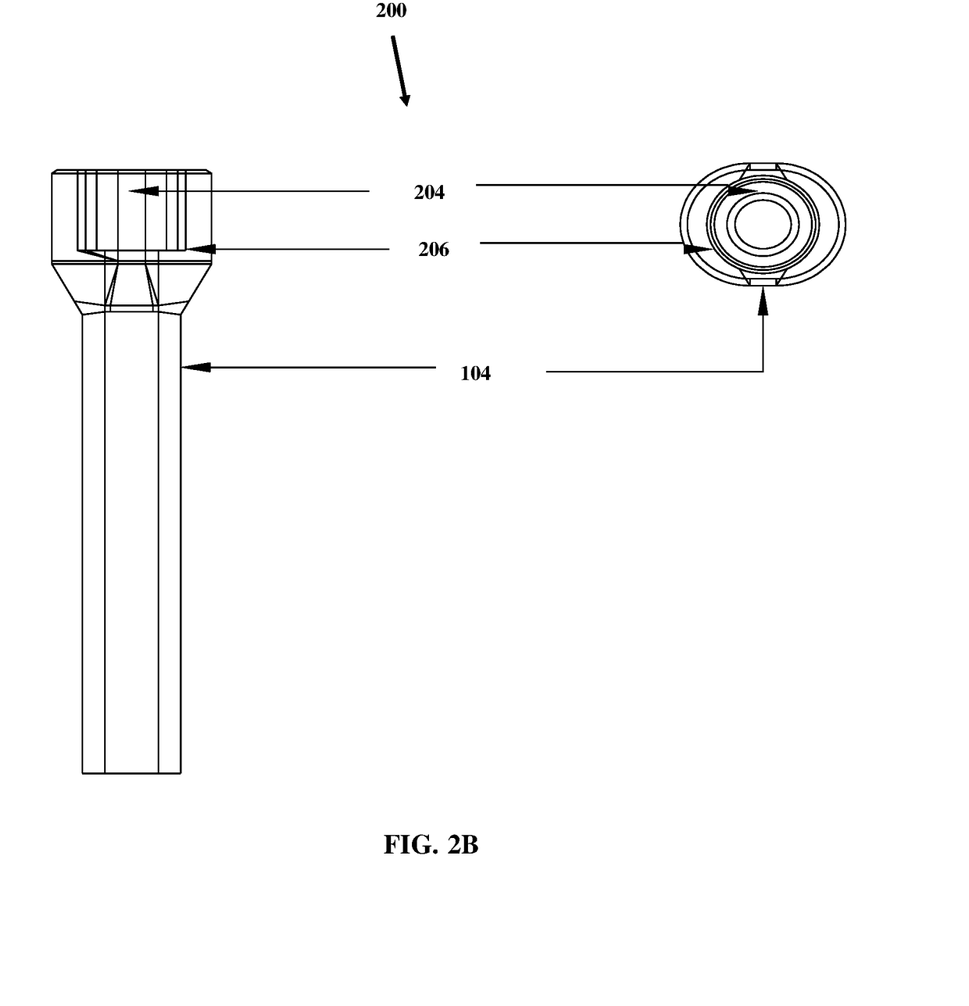
FIG. 2B illustrates a front view and a top view of the proposed bi-modal ultrasound-pressure sensor based arterial compliance probe, according to the embodiments as disclosed herein.

FIG. 2B illustrates a front view and a top view of the proposed bi-modal ultrasound-pressure sensor based arterial compliance probe (200), according to the embodiments as disclosed herein. This arterial compliance probe design (200) comprises a probe holder (202), a single element ultrasound transducer (204) connected to a first end of the probe holder (202), a bio-potential transducer (206) connected to a second end of the probe holder (202) and a controller connected to the bio-potential sensor (204) and single element ultrasound transducer (206).

In an embodiment, the bio-potential sensor (206) is one of a pressure sensor, a force sensor and another single element ultrasound transducer.

In an embodiment, the single element ultrasound transducer (206) can be replaced with any other measurement modalities such as photoplethysmography that can capture instantaneous or minimum to maximum arterial diameter/cross-sectional area/volume changes and is configured in an array configuration of linear/curvilinear/annular (refer the FIG. 2A) or concentric ultrasound-pressure transducer arrangement (refer the FIG. 2B). In an embodiment, the bio-potential sensor (204) are arranged in proximal to the single-element ultrasound transducer (206) or configured in one of a linear arrays configuration, a curvilinear arrays configuration, and an annular arrays configuration. In an embodiment, the bio-potential sensor (204) are arranged in concentric arrangement around the single-element ultrasound transducer (206). This can be used for simultaneous or sequential evaluation of arterial diameter and mechanical characteristics (using ultrasound sensor), and estimation of magnitude of blood pressure acting on the skin surface as well as the applied force (hold-down pressure) on the probe (using pressure/force sensor). These estimates would be used for evaluation of blood pulse wave velocity, and blood pressure with/without any subject-specific and/or population-specific calibration.

The single element ultrasound transducer (204) is configured to measure a change in arterial dimensions over a cardiac cycle. The bio-potential transducer (206) is configured to measure a bio-potential signal acting on the measurement site, wherein the bio-potential signal is a function of at least one of an arterial pressure level measured by the bio-potential sensor, an applied or hold-down pressure measured by the bio-potential sensor, and external factors acting during the measurement using the arterial compliance probe. Further, the controller is configured to measure the BP based on the change in arterial dimensions and the bio-potential signal.

Mathematical models: P-β Models for calibration-free cuffless BP evaluation: A generalized mathematical model that relates arterial pressure level (P) with the mechanical and geometrical characteristics of an arterial vessel segment is proposed; henceforth referred to as P-β model. The P-β model for calibration-free cuffless blood pressure (BP) measurement is developed using (1) Logarithmic relation between arterial blood pressure (P), arterial dimensions and stiffness index (β), given by equation 1;

$$\beta = \frac{\ln\left(\frac{P}{P_D}\right)}{\left(\frac{D - D_D}{D_D}\right)}, \quad (1)$$

(2) Bramwell-Hill equation of waves in liquid-filled elastic tubes, given by equation 2 (A is the arterial cross-sectional area);

$$\text{Local } PWV, C = \sqrt{\frac{A}{\rho}\frac{dP}{dA}}, \quad (2)$$

and (3) variation of local pulse wave velocity (PWV) within a cardiac cycle. The proposed general form of P-β equation is defined as the product of instantaneous BP level (P) and stiffness index (β) proportional to the square of instantaneous local PWV (C) and the ratio of the end-diastolic diameter (DD) to corresponding instantaneous diameter value (D) (refer equation 3).

$$P\beta = \frac{2\rho C^2 D_D}{D}, \quad (3)$$

Two practical models (P-β model I and P-β model II) are developed using the general P-β equation for calibration-free evaluation of arterial BP parameters without using any conventional bladder-type pressure cuff or its variants.

P-β model I equation is derived using the concept that, the ratio between arterial pressure level at any fiducial point (Ψ) in a cardiac cycle and the diastolic BP level of the same cardiac cycle is proportional to (1) the ratio of the square of local PWV at the selected fiducial point and local PWV at the diastolic point, (2) the ratio between end-diastolic diameter and arterial diameter at the selected fiducial point. This method relies only upon simultaneously acquired local PWV and diameter values from two distinct fiducial points within a cardiac cycle. Therefore, by directly measuring local PWV and diameter parameters from the end-diastolic point and any convenient fiducial point (Ψ), arterial stiffness index β can be evaluated from each cardiac cycle using equation 4.

$$\beta = \frac{\ln\left(\frac{C_\Psi^2 D_D}{C_D^2 D_\Psi}\right)}{\left(\frac{D_\Psi - D_D}{D_D}\right)}. \quad (4)$$

By substituting β into the proposed general form of P-β equation (refer equation 3) along with the local PWV and diameter parameters obtained from the end-diastolic point, diastolic BP (PD) level can be evaluated using equation 5.

$$P_D = \frac{2\rho C_D^2}{\beta} \quad (5)$$

Further, obtained PD and β can be substituted into the arterial pressure-diameter logarithmic expression to calculate systolic BP (PS) level (using equation 6).

$$P_S = P_D e^{\beta\left(\frac{\Delta D}{D_D}\right)} \quad (6)$$

P-β model II equation is derived from the general P-β model by re-arranging it in terms of arterial pressure and diameter gradient. The gradient is defined as the ratio between minimum to maximum change and the minimum value. Here, pulse pressure in each cardiac cycle is expressed in terms of diameter and local PWV at systolic peak point using the Bramwell-Hill equation. According to P-β model II, the diastolic BP level is directly proportional to the square of local PWV at the diastolic phase and diameter gradient, and inversely proportional to the logarithm of the pressure gradient. After measuring the arterial diameter gradient $$\left(\frac{\Delta D}{D_D}\right)$$

using any suitable technique such as ultrasound-based approach, the arterial pressure gradient $$\left(\frac{\Delta P}{P_D}\right)$$

can be directly evaluated. Here, $\Delta D$, $D_D$, $\Delta P$, and $P_D$ are arterial distension, end-diastolic diameter, pulse pressure, and diastolic BP level respectively. By measuring local PWV at the diastolic phase, diastolic BP level from each cardiac cycle can be estimated using P-β model II. Further, the product of estimated diastolic BP and pressure gradient gives pulse pressure, their numerical addition provides the systolic BP level. An estimate of local PWV at systolic phase can also be obtained from this model.

Accordingly the embodiments herein provides a system for cuff-less blood pressure measurement of a subject, the system comprising ultrasound-based arterial compliance probes and a controller unit connected to the said probe. The said probe consists of a unimodal or a bi-modal or a multi-modal arrangement of a pressure sensor or a force sensor or suitable bio-potential transducers along with a single element ultrasound transducer. The ultrasound transducers are configured to measure a change in arterial dimensions (includes arterial diameter waveforms, minimum and maximum diameter, diameter at any given point, arterial wall thickness waveform, minimum and maximum arterial thickness values, arterial wall thickness value at any given point) over a cardiac cycle. The pressure sensor/force sensor/bio-potential transducers are configured to measure a pressure acting on a skin surface at a measurement site, an internal arterial transmural pressure level, an applied pressure or hold-down pressure of the said arterial compliance probe acting on the skin surface or arterial site, a biopotential and/or plethysmograph signal acting on the measurement site as function of arterial pressure and/or function of the applied/hold-down pressure and/or function of external factors acting during the measurement using said arterial compliance probe.

In an embodiment, the arrangement of arterial compliance probe (unimodal, dual-element probe) comprises a first ultrasound sensor and a second ultrasound sensor; said second ultrasound sensor separated by known fixed or variable distance from said first ultrasound sensor with 0 to 360 degree of relative angle between said first sensor and second sensor, and operated simultaneously or sequentially. Further, said first sensor and second sensor configured in parallel orientation to measure arterial dimensions of a subject by tracking the motion of said arterial wall from one ultrasound frame to a subsequent ultrasound frame. The first sensor detects arterial diameter waveform first site along said artery wall, second sensor detects arterial diameter waveform second distinct site along the artery wall; and measurement of said arterial diameter parameters (including minimum and maximum diameter values, intermediate value at any fiducial point) and local pulse wave velocity and, variation in local pulse wave velocity as function of arterial diameter or arterial pressure level from distinct fiducial points by computing time difference between said fiducial points of diameter waveform captured from said first site and second site.

In another embodiment, the arrangement of said arterial compliance probe, said first sensor is arranged and placed perpendicular to said arterial wall of a subject, wherein said second sensor is configured with a relative angle (between 0 to 360 degree) with respect to the first sensor; simultaneously or sequentially measuring arterial dimensions, diameter waveforms, blood flow waveform, cross-sectional area variations, Doppler velocity and, geometrical, mechanical and flow characteristics from the said artery/arterial segments of the subject by tracking subsequent ultrasound echo frames; and used to measure diameter parameters and local pulse wave velocity from the measurement site of the subject.

In another embodiment, the arrangement of said arterial compliance probe (bi-modal ultrasound-pressure sensor-based design) comprising the pressure or force sensor (non-calibrated to obtain instantaneous waveforms and/or calibrated to procure instantaneous waveforms and absolute pressure/force values) arranged proximal to single-element ultrasound transducer, or configured in an array configuration (linear/curvilinear/annular).

In another embodiment, additional arrangement of said arterial compliance probe (bi-modal ultrasound-pressure sensor-based design) comprising ring-shaped pressure or force sensor (non-calibrated to obtain instantaneous waveforms and/or calibrated to procure instantaneous waveforms and absolute pressure/force values) arranged in concentric ultrasound-pressure transducer arrangement with ultrasound sensor in the middle of the concentric ultrasound-pressure transducer arrangement; or in another arrangement with pressure/force sensor in the middle of the concentric ultrasound pressure-transducer arrangement.

Further, the ultrasound-pressure transducer arrangement of arterial compliance probe performs simultaneous/sequential/continuous/periodic measurement of arterial dimensions using said single-element ultrasound transducer along with the measurement of arterial compliance probe placement pressure (on the skin surface); hold-down pressure; blood pressure acting on the skin surface; transmural blood pressure, provides feedback to the controller unit to guide operator, utilized to extract the transfer function of the tissue layer at the measurement site (between skin surface arterial segment), utilized to develop characteristic blood pressure-area curve; blood-pressure diameter curve; blood pressure-volume curve, utilized to estimate blood pressure parameters of the said subject.

Accordingly the embodiments herein provides a method and hand-held device with arterial compliance probe for the evaluation of arterial dimensions including diameter parameter, arterial wall thickness and local pulse wave velocity, blood flow velocity, and Doppler velocity waveform using single-element ultrasound transducer.

In an embodiment, the evaluation of arterial blood pressure that utilizes the linear or non-linear relationship between the blood pressure values at multiple points within a cardiac cycle to the corresponding values of pulse wave velocity and diameter (or cross sectional area) at multiple points within a cardiac cycle, including but not limited to the systole and diastole points.

In an embodiment, the evaluation of arterial blood pressure which utilizes real-time measurements of arterial diameter gradient $$\left(\frac{\Delta D}{D_D}\right)$$

evaluate the pressure gradient $$\left(\frac{\Delta P}{P_D}\right)$$

and measurements of PWV from multiple points in the cardiac cycle to estimate the arterial pressure.

In an embodiment, the evaluating arterial blood pressure by utilizing the change in pulse wave velocity from systole to diastole within a cardiac cycle, along with measurements of arterial dimensional changes for calculating an arterial pressure waveform.

In an embodiment, the evaluation of arterial BP that uses ultrasound sensors/transducers to evaluate arterial dimensions and pulse wave velocity from any artery, and employment of any of the techniques/methods for evaluation of blood pressure.

In an embodiment, the evaluation of blood pressure that utilizes the real-time changes in arterial dimensions over a cardiac cycle and simultaneous measurement of beat-to-beat heart rate/pulse rate to estimate a surrogate of cardiac output which is then calibrated to obtain an estimate of blood pressure.

Figure 3:
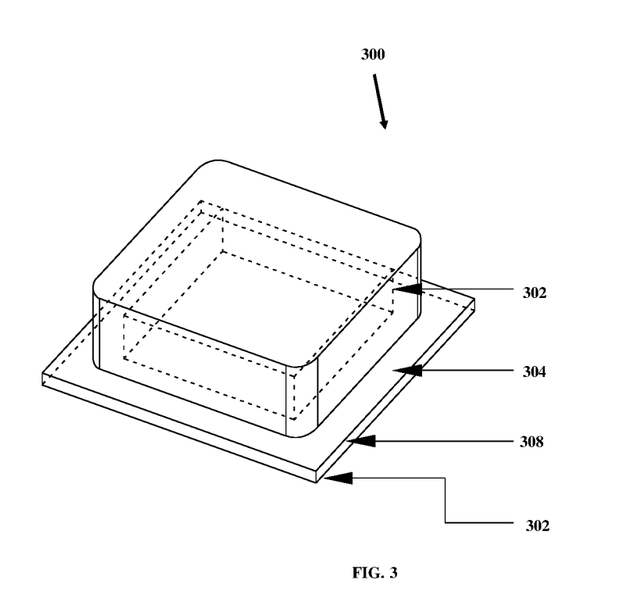
FIG. 3 illustrates a single-element accelerometric sensing element, according to the embodiments as disclosed herein.

FIG. 3 illustrates a single-element accelerometric sensing probe (300), according to the embodiments as disclosed herein.

Figure 4:
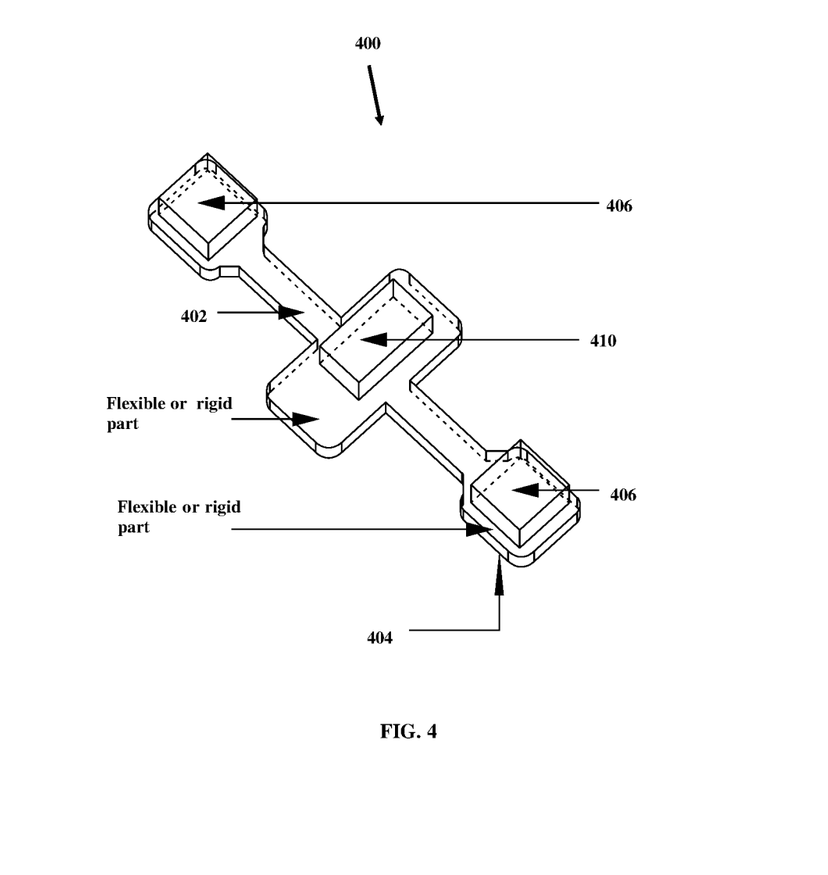
FIG. 4 illustrates multi-element accelerometric sensing element, according to the embodiments as disclosed herein.

FIG. 4 illustrates multi-element accelerometric sensing probe (300), according to the embodiments as disclosed herein.

The accelerometric sensing probe (300) comprises an adhesive material (302), at least one accelerometer (306), and a printed circuit board (308) connected to the at least one accelerometer (306). The adhesive material (302) configured to stick the arterial compliance probe on a measurement site of the subject. The at least one accelerometer is covered with a protective case (304). The adhesive material (302) is attached on the printed circuit board (308) to stick the arterial compliance probe (300) on the measurement site of the subject. The at least one accelerometer (306) configured to measure a change in arterial dimensions and an acceleration signal associated with arterial wall displacement towards the measurement site caused by propagation of blood pulses, and the printed circuit board (308) configured to locally measure arterial vessel wall dynamics and arterial blood pressure parameters of the subject based on the change in the arterial dimensions and the acceleration signal, and measure the BP of the subject based on the arterial vessel wall dynamics and the arterial blood pressure parameters.

In an embodiment, the arterial vessel wall dynamics comprises at least one of arterial compliance, a stiffness index, a distensibility, and Young's elastic modulus.

Accelerometer-based system for vascular wall stiffness indices and blood pressure evaluation: A method and system for non-invasive evaluation of vascular wall stiffness indices and arterial blood pressure parameters using single- or multi-element accelerometers or accelerometric sensors (refer the FIG. 3 and the FIG. 4) is devised. Vibrations/acceleration of the skin surface above any superficial artery produced by the arterial wall displacement due to the acceleration associated with arterial wall displacement towards the skin surface caused by the propagation of the blood pulses are captured (continuous and/or periodically) using the developed sensing modules/transducer elements. The proposed accelerometer-based system (or accelerometric system) and the associated sensing elements can be a handheld device and/or wearable device/patch—either wired or wireless. The designed accelerometric system can continuously acquire the arterial wall displacement waveform by double integration of the accelerometer signal acquired from the measurement site. Acceleration plethysmograph (APG) signals acquired using a single-element accelerometric sensing element (refer the FIG. 3) is used to determine arterial diameter parameters (through desired one-time or periodic device or subject- and/or population-specific calibration), and hence the vascular wall stiffness indices such as (not limited to) arterial compliance, stiffness index, distension and Young's elastic modulus. These estimates can be substituted in the proposed mathematical models to further evaluate blood pressure parameters.

A duality of accelerometric sensing elements arranged at known fixed or variable distance in the form of a wearable arterial compliance probe (400) or patch is an optimized arrangement for the two-point method based PWV measurement (refer the FIG. 4). In this wearable probe (400) comprises a flexible band (402), an adhesive material (404) a first accelerometer (406) attached to the adhesive material (402), and a second accelerometer (408) attached at a second end of the flexible band (402), and a controller (410) connected between the first accelerometer (406) and the second accelerometer (408).

The adhesive material (404) is used to worn the arterial compliance probe (400) on a measurement site of the subject. The first accelerometer (406) is configured to measure a first acceleration signal acquired from a first fiducial point of the measurement site. The second accelerometer (408) configured to measure a second acceleration signal acquired from a second fiducial point different the first fiducial point of the measurement site. Further, the controller (410) is configured to measure a local pulse wave velocity and change in arterial dimensions based on a time difference between the first acceleration signal and the second acceleration signal, and measure the BP of the subject based on the local pulse wave velocity and the change in the arterial dimensions. This arrangement or a similar one with suitable modifications in the probe/patch can be used for PWV evaluation from a PWV). Local PWV and diameter parameters obtained from accelerometer-derived wall displacement waveforms is appropriate for non-invasive, cuffless and continuous evaluation of arterial blood pressure parameters by the use of the proposed P-β models. Such an arrangement and/or blood pressure monitors can be integrated to portable and wearable monitors, which can be used for continuous and 24-hours ambulatory blood pressure measurement, without the need of any bladder-type pressure cuff.

Accordingly the embodiments herein provides a patch probe/wearable sensor arrangement for vascular wall stiffness indices and blood pressure evaluation of a subject, comprising a patch probe configured to stick to the skin above the superficial arteries of a subject as described in the FIG. 3. The said probe comprises of single-element accelerometers or accelerometric sensors configured to measure the change in arterial dimensions and the acceleration associated with arterial wall displacement towards the skin surface caused by the propagation of the blood pulses wherein, said acceleration plethysmograph signal and derivatives, and/or integral of the said signal are used to develop transfer function of the tissue layer between the skin surface and the arterial site under measurement of the said subject. Extracting said transfer function of the measurement site, the system configured to measure (non-invasively and continuously) arterial vessel wall dynamics (including but not limited to arterial compliance, stiffness index, distensibility, Young's elastic modulus) and arterial blood pressure parameters of said subject locally.

In an embodiment, the patch probe/wearable sensor arrangement for vascular wall stiffness indices and blood pressure evaluation of a subject, comprising a patch probe configured to stick on the skin above the superficial arteries of a subject. The said probe has a duality (first sensor and second sensor) of accelerometers or accelerometric sensors placed at a known fixed or variable distance; configured to measure change in arterial dimensions and the acceleration associated with arterial wall displacement towards the skin surface caused by the propagation of the blood pulses from first and second arterial sites. The said first sensor and second sensor are configured to measure a local pulse wave velocity from acceleration plethysmograph signal acquired from said first measurement site and acceleration plethysmograph signal acquired from said second measurement site by computing time difference between fiducial points of acceleration plethysmograph signal captured from said first site and second site. The said local PWV and change in arterial dimensions obtained using the accelerometers or accelerometric sensors are used to measure blood pressure parameters of the subject in non-invasive and continuous manner.

The embodiments disclosed herein can be implemented using at least one software program running on at least one hardware device and performing network management functions to control the elements.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. An arterial compliance probe for cuff-less measurement of blood pressure (BP) of a subject, the arterial compliance probe comprising:
   a probe holder to apply the arterial compliance probe on a measurement site of the subject;
   a first ultrasound transducer, connected at a first end of the probe holder, configured to measure a first arterial dimension waveform at a first fiducial point of the measurement site of the subject;
   a second ultrasound transducer, connected to a second end of the probe holder, configured to measure a second arterial dimension waveform at a second fiducial point different than the first fiducial point of the measurement site of the subject,
      wherein the first arterial dimension waveform and the second arterial dimension waveform are measured within a cardiac cycle; and
   a controller, connected to the first ultrasound transducer and the second ultrasound transducer, configured to:
      measure an arterial dimension parameter within the cardiac cycle from the first arterial dimension waveform and the second arterial dimension waveform,
      measure a variation in a local pulse wave velocity within the cardiac cycle based on a time difference between the first arterial dimension waveform and the second arterial dimension waveform,
      measure a stiffness property of an artery based on the variation in the local pulse wave velocity, and
      measure the BP of the subject based on the variation in the local pulse wave velocity, the stiffness property, and the arterial dimension parameter.

2. The arterial compliance probe of claim 1, wherein the first ultrasound transducer and the second ultrasound transducer are configured in parallel orientation to measure the first arterial dimension waveform and the second arterial dimension waveform of the subject by tracking a motion of arterial walls at the measurement site from one ultrasound frame to a subsequent ultrasound frame.

3. The arterial compliance probe of claim 1, wherein the first ultrasound transducer is separated by fixed or variable distance from the second ultrasound transducer.

4. The arterial compliance probe of claim 1, wherein the first ultrasound transducer and the second ultrasound transducer are operated simultaneously or sequentially.

5. The arterial compliance probe of claim 1, wherein the first ultrasound transducer and the second ultrasound transducer are arranged and placed perpendicular or non-perpendicular to the measurement site of the subject with a relative angle between the first ultrasound transducer and the second ultrasound transducer.

6. The arterial compliance probe of claim 1, wherein the first arterial dimension waveform and the second arterial dimension waveform comprises at least one of the diameter waveform, blood flow waveform, cross-sectional area waveform, Doppler velocity and, arterial wall thickness waveform, geometrical, mechanical and flow characteristics from segments of the measurement site of the subject by tracking a subsequent ultrasound echo frames.

7. The arterial compliance probe of claim 1, wherein the first ultrasound transducer and the second ultrasound transducer comprises one of a single element or a plurality of elements used for real-time measurement of the first arterial dimension waveform and the second arterial dimension waveform.

8. The arterial compliance probe of claim 7, wherein the plurality of elements are configured in one of a linear array configuration, a curvilinear array configuration, and an annular array configuration.

* * * * *